United States Patent
Buijs (10) Patent No.: US 10,101,271 B2
(45) Date of Patent: Oct. 16, 2018

(54) MEASUREMENT OF HYDROCARBON CONTAMINATION IN WATER

(71) Applicant: ABB Schweiz AG, Baden (CH)

(72) Inventor: Henry L. Buijs, Quebec (CA)

(73) Assignee: ABB Schweiz AG, Baden (CH)

( * ) Notice: Subject to any disclaimer, the term of this patent is extended or adjusted under 35 U.S.C. 154(b) by 0 days.

(21) Appl. No.: 15/387,032

(22) Filed: Dec. 21, 2016

(65) Prior Publication Data

US 2018/0172586 A1     Jun. 21, 2018

(51) Int. Cl.
    *G01N 21/59*      (2006.01)
    *G01N 33/18*      (2006.01)

(52) U.S. Cl.
    CPC ......... *G01N 21/59* (2013.01); *G01N 33/1833* (2013.01)

(58) Field of Classification Search
    CPC .......................... G01N 21/59; G01N 33/1833
    See application file for complete search history.

(56) References Cited

U.S. PATENT DOCUMENTS

| | | | |
|---|---|---|---|
| 3,806,727 A | 4/1974 | Leonard et al. | |
| 4,674,879 A | 6/1987 | Gregorig et al. | |
| 6,373,567 B1 * | 4/2002 | Wise | G01J 3/1838 356/301 |
| 8,445,841 B2 | 5/2013 | Szobota et al. | |
| 2003/0071216 A1 * | 4/2003 | Rabolt | G01J 3/02 250/339.02 |
| 2013/0037719 A1 | 2/2013 | Melling et al. | |
| 2015/0276588 A1 | 10/2015 | Marshall et al. | |
| 2017/0016813 A1 * | 1/2017 | Wagner | G01N 21/3577 |

* cited by examiner

*Primary Examiner* — Hugh H Maupin
(74) *Attorney, Agent, or Firm* — J. Bruce Schelkopf; Taft Stettinius & Hollister LLP (57) ABSTRACT

A method for performing infrared analysis for measuring hydrocarbon contamination in water includes providing light from a light source; directing light from the light source through an experimental water sample; detecting the light transmitted from the experimental water sample; and determining a level of hydrocarbon contamination in the experimental water sample based on the light loss in the range between about 5700 cm$^{-1}$ and 6300 cm$^{-1}$. An apparatus for performing infrared analysis for measuring hydrocarbon contamination in water includes a controller operative to determine light loss through the sample cell and to determine a level of hydrocarbon contamination in the experimental water sample based on the light loss in the range between about 5700 cm$^{-1}$ and 6300 cm$^{-1}$.

33 Claims, 4 Drawing Sheets

MEASUREMENT OF HYDROCARBON CONTAMINATION IN WATER

TECHNICAL FIELD

The present application generally relates to hydrocarbon contamination and more particularly, but not exclusively, to an apparatus and method for measuring hydrocarbon contamination in water.

BACKGROUND

Methods and apparatuses for measuring hydrocarbon contamination in water remain an area of interest. Some existing apparatuses have various shortcomings, drawbacks and disadvantages relative to certain applications. For example, with some methods and apparatuses, a current method for measuring hydrocarbon contamination in water employs solvent or membrane extraction of the hydrocarbon from a known quantity of water, followed by determination of the hydrocarbon quantity by infrared analysis of the extracted hydrocarbon using an infrared transparent solvent, such as chlorofluorocarbon, which is time consuming. Accordingly, there remains a need for further contributions in this area of technology.

SUMMARY

One embodiment of the present invention is a unique method for performing infrared analysis for measuring hydrocarbon contamination in water. Another embodiment is a unique apparatus for performing infrared analysis for measuring hydrocarbon contamination in water. Other embodiments include apparatuses, systems, apparatuses, devices, hardware, methods, and combinations for infrared analysis of oil contamination in water. Further embodiments, forms, features, aspects, benefits, and advantages of the present application shall become apparent from the description and figures provided herewith.

BRIEF DESCRIPTION OF THE FIGURES

The description herein makes reference to the accompanying drawings wherein like reference numerals refer to like parts throughout the several views, and wherein.

DETAILED DESCRIPTION OF THE ILLUSTRATIVE EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1:
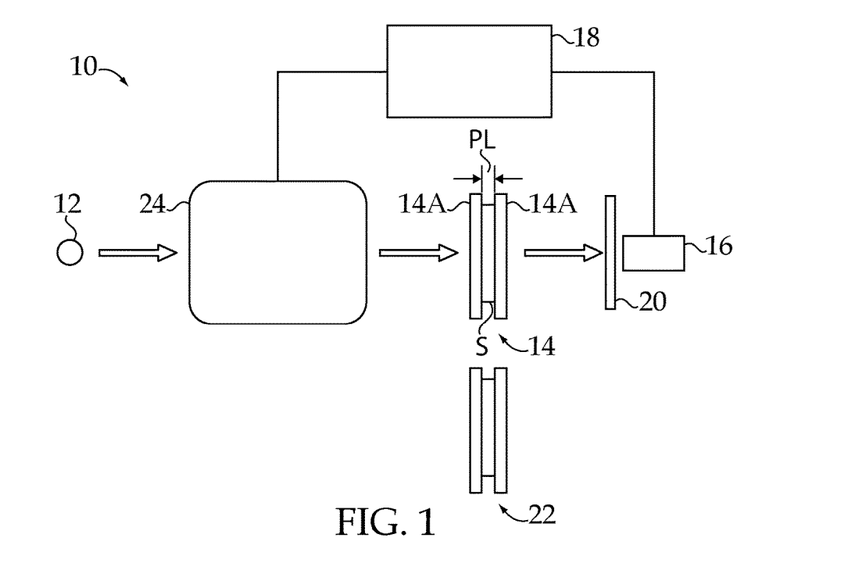
FIG. 1 schematically illustrates some aspects of a non-limiting example of an apparatus for measuring hydrocarbon contamination in water in accordance with an embodiment of the present invention.

Referring to FIG. 1, some aspects of a non-limiting example of an apparatus 10 for measuring hydrocarbon contamination in water in accordance with an embodiment of the present invention are schematically illustrated. Apparatus 10 includes a light source 12, a sample cell 14; a detector 16 and a controller 18. Some embodiments may include a filter 20, e.g., disposed in the optical path between the sample cell and detector 16. Other embodiments may not include a filter or may include other filters in addition to or in place of filter 20. In some embodiments light source 12 may include one or more filters, or one or more filters may be disposed between light source 12 and the sample cell, so that the sample cell receives light at only one or more desired wavelengths or wavelength bands. Some embodiments may include a second or subsequent sample cell(s) 22, whereas other embodiments may employ only a single sample cell. Some embodiments may include a spectroscope, spectrometer, spectrum analyzer, dispersive diode array spectrometer, tunable wavelength source or device or tunable laser 24.

Apparatus 10 is operative to measure hydrocarbon contamination in water, e.g., oil and/or grease contamination in water, by passing light through an experimental sample contained within sample cell 14 (e.g., the experimental sample being a water sample that is contaminated or potentially contaminated with hydrocarbons, such as trace hydrocarbon amounts or greater), and by analyzing the light transmitted through the sample to determine the light loss at particular wavelengths or reciprocal wavelengths expressed as wavenumbers or frequencies or within a range of frequencies or wavenumbers in the near infrared (NIR) spectrum. In some embodiments, the results of the experimental sample analysis are compared with the results of an infrared analysis of a reference sample, e.g., pure water, in order to determine the presence of, and in some embodiments, the amount of hydrocarbon contamination. For example, the light loss associated with the reference sample at particular wavenumbers may be subtracted from the light loss associated with the experimental sample at the same wavenumbers, thus yielding light loss associated with the impurities in the experimental sample. As discussed herein, the NIR wavenumbers which are analyzed are those associated with hydrocarbon absorption, and hence, light loss associated with those frequencies is reflective of hydrocarbon contamination. In some embodiments, sample cell 14 may be used to sequentially analyze the reference sample and the experimental sample, e.g., by analyzing the reference sample, flushing the reference sample out of the sample cell and replacing it with the experimental sample, and subsequently analyzing the experimental sample. Other embodiments may reverse the order of analysis.

In some embodiments, the experimental sample may be contained in sample cell 14 and the reference sample may be contained in sample cell 22, and the samples may be analyzed separately. For example, some embodiments may employ a single optical path, and may sequentially analyze the samples, e.g., by analyzing a reference sample in sample cell 14, wherein sample cell 14 being disposed within the optical path; replacing sample cell 14 with sample cell 22 containing an experimental sample, so that sample cell 22 is disposed within the optical path; and then analyzing the experimental sample. The order may be reversed in other embodiments. In some embodiments, dual optical paths, each having the same optical characteristics, may be employed, eliminating the need for replacing the sample cells.

Spectral analysis in some embodiments of the present invention includes directing light generated by an infrared source, e.g., light source 12, through a sample and measuring the loss of light by the sample for different wavelengths, e.g., as determined by means of a spectrometer or spectrum analyzer that separates the light into different wavelengths or frequencies, and an infrared detector that converts the light into measurable signals. In some embodiments, the loss of light by the sample is isolated from other variations in light intensity by use of a reference spectrum, e.g., the analysis of the reference sample, such as a pure water sample in the same sample cell or the same type of sample cell, i.e., having the same optical characteristics. For example, as mentioned above, analysis of the reference sample may employ the same optical path, except for the absence of the experimental sample, which in some embodiments is replaced with the reference sample. If impurities in an experimental sample are to be determined, such as oil or other hydrocarbon impurities in water, a pure water sample may be employed as a reference sample.

Figure 2:
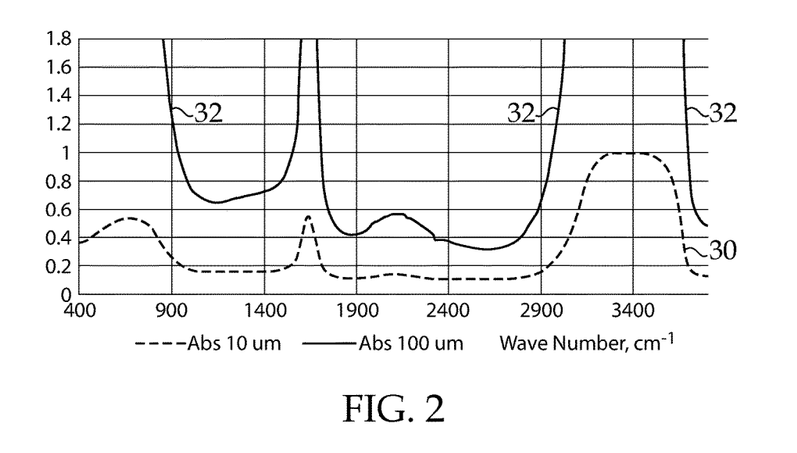
FIG. 2 is a plot illustrating some aspects of a non-limiting example of water absorbance in the near infrared spectrum based on 10 μm and 100 μm sample path lengths.

While it is possible to measure hydrocarbon contamination in water using infrared analysis, previous apparatuses and methods do not allow the direct measurement of very low concentrations, e.g., trace amounts measured in the tens of parts per million (ppm) or less. For example, a 10 micrometer (0.01 mm) film of water is infrared transparent over a wide spectral range and can be analyzed by general infrared transmission spectroscopy. A sample of water-hydrocarbon mixture can be analyzed by infrared analysis when the infrared beam path length through the sample is restricted to 10 micrometers or less. By the Beer-Lambert law the measured absorbance is proportional to the concentration of the absorbing medium and the thickness. The path length being very low (e.g., 10 μm) for water samples, only relatively high concentrations of hydrocarbons can be measured by general infrared transmission spectroscopy. Typical measurable hydrocarbon concentrations in water are >1%. Current infrared spectrometers do not have the extraordinarily high sensitivity and stability that would be required to extend the measurable hydrocarbon concentrations down to trace amounts or ppm levels using existing methodology. Trace amounts or ppm levels of hydrocarbon contamination in water includes contamination in the range of, for example, tens of ppm, i.e., 100 ppm or less, and in some cases as low as 1-20 ppm (0.0001%-0.0020%) or less. Increasing the infrared beam path length to, for example, 100 micrometers (0.1 mm) may permit the measurement of lower concentrations of hydrocarbons, but, unfortunately, water may no longer be transparent at higher water sample path lengths, which may impair or prevent measurement of trace amounts of hydrocarbon contamination using existing methodologies. For example, with reference to FIG. 2, water absorbance at 10 μm and 100 μm path lengths are illustrated, indicated by reference characters 30 and 32, respectively. Although increasing the path length from 10 μm to 100 μm may yield measurement of 10× lower concentrations of hydrocarbon contamination, the water sample is no longer transparent over a wide spectral range and the infrared analysis capability may be significantly diminished. It will be understood that further increases in the sample path length will further and substantially reduce the spectral regions where the water sample is transparent, and further impair or prevent measurement of lower amounts of contamination using existing methodologies.

Conventionally, the practice of determining ppm level concentrations of hydrocarbons in water includes first extracting the hydrocarbon from a known quantity of water and then carrying out a determination of the quantity of hydrocarbon extracted. Extraction can be done by solvent extraction, or membrane extraction, for example. Using an infrared transparent solvent, such as a chlorofluorocarbon (CFC), permits determination of extracted hydrocarbon by infrared analysis using several cm path length through the CFC sample.

The inventors have determined that a particular region within the NIR spectrum may be particularly useful for infrared analysis of trace levels of hydrocarbon contamination in water, without requiring the time consuming step of extracting the hydrocarbons from the water prior to analysis.

In one form, apparatus 10 is constructed to measure low levels of spectrally resolved absorbance, e.g., such as for example an FT IR spectrometer in conjunction with a suitably bright infrared source and a suitably sensitive infrared detector element or a suitably stable tunable laser or other device capable of providing highly sensitive and stable spectrometric data. By increasing the path length through the water and hydrocarbon sample such that extensive parts of the infrared spectrum are no longer transparent, while retaining a limited spectral region of transparency coincident with a spectral region where the majority of hydrocarbons (oils, fats and greases) have characteristic absorption bands, the measurement of trace hydrocarbon contamination may be performed. For example, referring to FIGS. 2-5, although it may be considered that one of the strongest characteristic spectral absorption bands attributed to many hydrocarbons is the C—H stretch band at approximately 3450 nm (2900 cm-1), in this spectral region the water absorption (FIG. 2) is still very high due to the broad nature of the O—H stretch band of water at 2770 nm (3600 cm$^{-1}$), and hence this does not provide a favorable spectral region for the trace or ppm level determination of hydrocarbon contamination in water.

Figure 3:
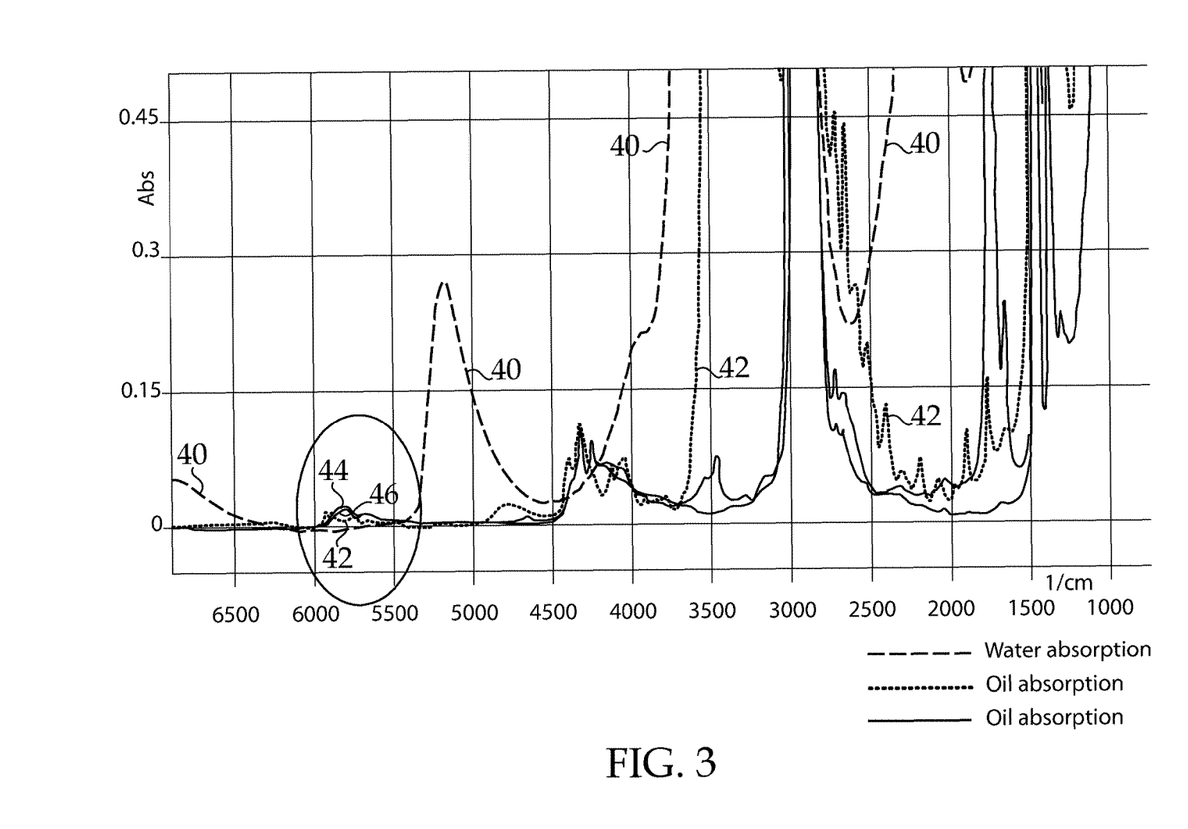
FIG. 3 is a plot illustrating some aspects of a non-limiting example of water absorption and hydrocarbon absorption in the near infrared spectrum highlighting a region of low water absorption and high hydrocarbon absorption.
Figure 4:
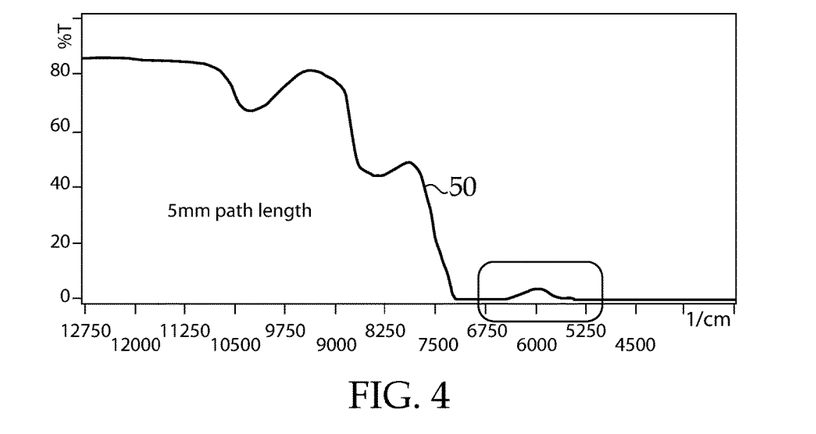
FIG. 4 illustrates some aspects of a non-limiting example of a transmittance spectrum of a 5 mm path length water sample in the near infrared, providing about 5% transmittance in the approximately 5700 $cm^{-1}$ to 6300 $cm^{-1}$ region.
Figure 5:
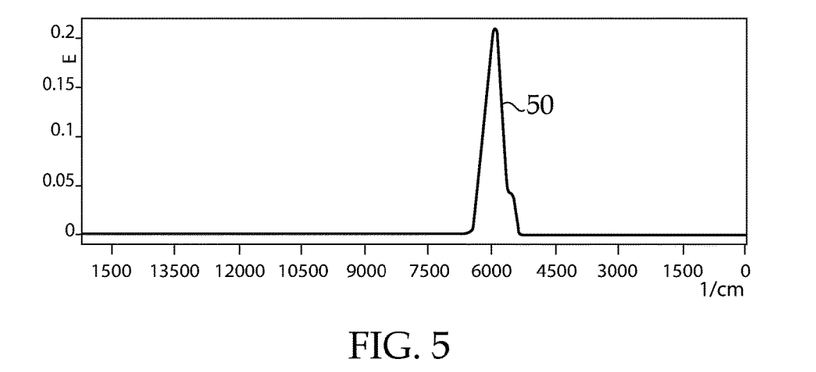
FIG. 5 illustrates some aspects of a non-limiting example of a transmittance region at approximately 5700 $cm^{-1}$ to 6300 $cm^{-1}$ defined by water absorption on both the high and low frequency side of the region.

On the other hand the first harmonic of the C—H stretch band at 1770 nm (5700 cm$^{-1}$) in the near infrared is strong compared with the residual water absorption in this region. The sample path length is maximized by limiting the water transmission to a small but adequate level so that the lowest concentration of hydrocarbons can be measured. FIG. 3 illustrates water absorption 40 and hydrocarbon absorption 42, 44 and 46 for three different hydrocarbons. As illustrated in FIG. 3, the region of approximately 5700 cm$^{-1}$ to approximately 6300 cm$^{-1}$, and in particular, the region of approximately 5700 cm$^{-1}$ to approximately 6000 cm$^{-1}$, i.e., which includes the C—H stretch first overtone, is a region that includes not only relatively low water absorption, but also includes a region of relatively high hydrocarbon absorption, wherein the ratio of hydrocarbon absorbance to water absorbance is the greatest. On an absolute scale, the hydrocarbon absorption is low in these regions, and thus not a conventionally desirable region for infrared analysis using existing methodologies. However, the inventors have discovered that the relatively high ratio of hydrocarbon absorbance to water absorbance in this region, not previously exploited, allows the measurement of trace levels of hydrocarbon contamination. FIGS. 4 and 5 illustrate transmittance 50 for a 5 mm path length water sample, wherein the water transmittance is approximately 5% in the region of 5700 $cm^{-1}$. The absorbance of the C—H stretch first overtone (e.g., of hydrocarbons) is much stronger than near infrared bands at shorter wavelengths and hence the high transmittance at frequencies higher than 7000 $cm^{-1}$ in FIG. 4 is not useful. Some embodiments employ an optical filter, e.g., optical filter 20, such as a 1500 nm long wave filter, which blocks the region above about 7000 $cm^{-1}$, yielding a narrow region of transmittance near approximately 5700 $cm^{-1}$ to approximately 6300 $cm^{-1}$, as illustrated in FIG. 5. In FIGS. 4 and 5, the region below the C—H stretch overtone, e.g., below about 5500 $cm^{-1}$, is also filtered out for the sake of clarity. The high ratio of hydrocarbon absorbance to water absorbance around the first harmonic for the C—H stretch overtone allows for greater infrared analysis sensitivity to low or trace hydrocarbon contamination quantities, particularly when the path length is increased, e.g., to 5 mm, allowing the measurement of trace amounts of hydrocarbon contamination in the low ppm range, e.g., down to 5 ppm or less in some embodiments, and down to 1 ppm or less in other embodiments.

Figure 6:
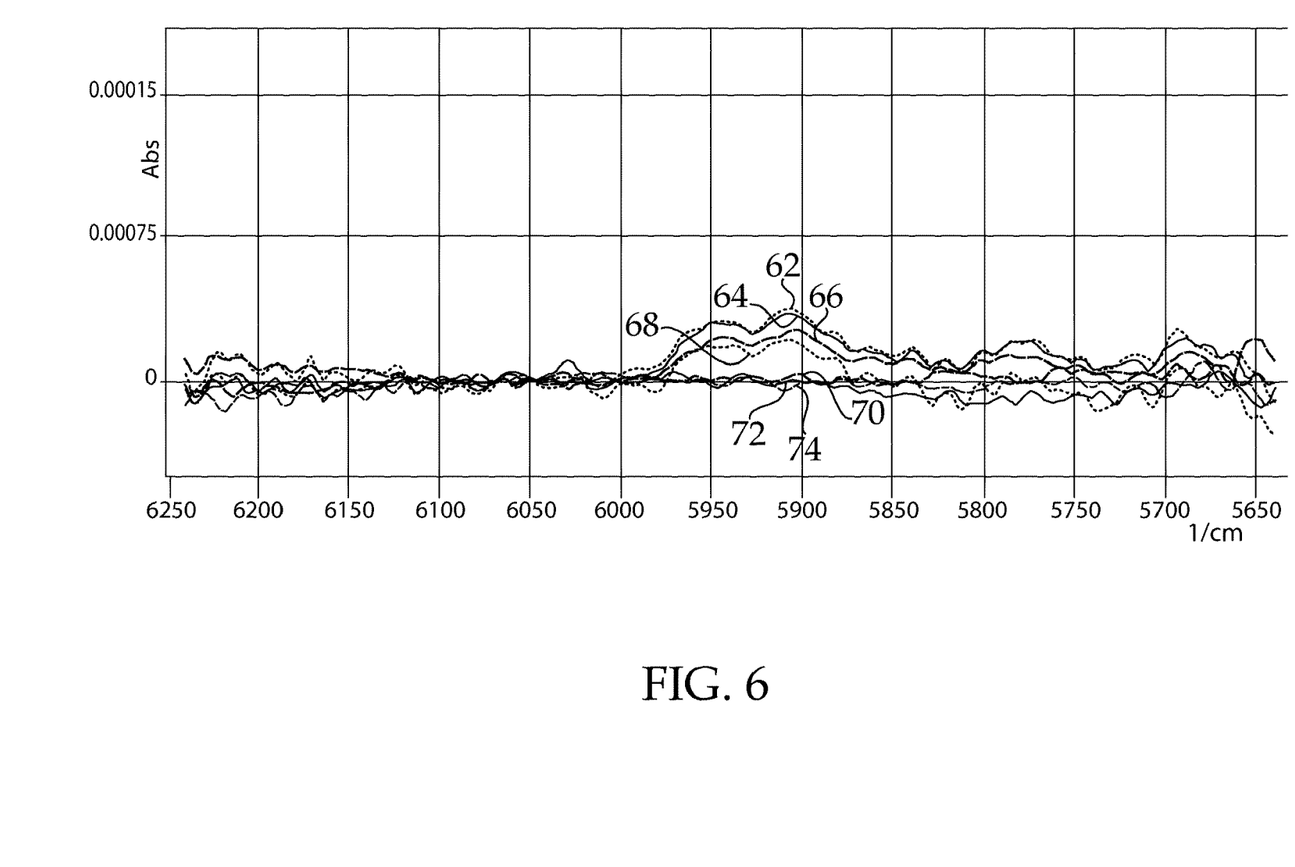
FIG. 6 illustrates some aspects of a non-limiting example of absorbance spectra for four (4) traces of 20 ppm isopropanol in water and three (3) traces of absorbance for pure water.

With reference to FIG. 3, although hydrocarbon absorption in the range of about 4200 $cm^{-1}$ to 4400 $cm^{-1}$ is greater in an absolute sense than in the region of approximately 5700 $cm^{-1}$ to approximately 6300 $cm^{-1}$, the ratio of hydrocarbon absorption to water absorption in the range of about 4200 $cm^{-1}$ to 4400 $cm^{-1}$ is not nearly as great as the ratio of hydrocarbon absorption to water absorption in the region of approximately 5700 $cm^{-1}$ to approximately 6300 $cm^{-1}$, particularly in the region of about 5700 $cm^{-1}$ to approximately 6000 $cm^{-1}$, which makes the latter NIR regions particularly suitable for detecting down to trace amounts of hydrocarbon contamination. The total absorption of radiation outside the small region of transmittance near approximately 5700 $cm^{-1}$ to approximately 6300 $cm^{-1}$ is favorable for an FTIR spectrometer avoiding overloading and excess noise when employing a sensitive near infrared detector. FIG. 6 illustrates absorbance spectra of four (4) traces 62, 64, 66, 68 of 20 ppm isopropanol in water and three (3) traces 70, 72, 74 of absorbance for pure water with a 5 mm sample path length. The detection limit in the example of FIG. 6 is estimated at <5 ppm. It will be understood that lower detection limits may be achieved in other embodiments, e.g., depending upon the light source characteristics and the detector characteristics, and spectrometer characteristics for embodiments so equipped.

Accordingly, embodiments of the present invention are directed to performing infrared analysis of water samples in the spectral range of approximately 5700 $cm^{-1}$ to approximately 6300 $cm^{-1}$, or wavenumber range between approximately 5700 and 6300. In some embodiments, the infrared analysis is performed only at frequencies in the wavenumber range between approximately 5700 and 6300. In some embodiments, a more narrow region may be employed, e.g., infrared analysis at or only at wavenumbers between approximately 5700 and 6000.

Light source 12 is operative to supply light or radiation to sample cell 14 for infrared analysis of the sample disposed within sample cell 14, including light in the NIR spectrum in between approximately 5700 $cm^{-1}$ and 6300 $cm^{-1}$. Light outside this range may also be supplied by light source 12. In one form, light source 12 is a filament-based incandescent light source, e.g., a commercially available quartz halogen light bulb, such as a quartz halogen automotive light bulb. In other embodiments, light source 12 may take other forms, and may be, for example, one or more lasers and/or light emitting diodes (LEDs) or any light source capable of producing infrared light across range between approximately 5700 $cm^{-1}$ and 6300 $cm^{-1}$, and in some embodiments, across the range between approximately 5700 $cm^{-1}$ and 6000 $cm^{-1}$.

Spectroscope 24 is constructed to modulate the frequency of the light received from light source 12. For example, spectroscope 24 is constructed to separate the light into separate frequencies or wavelengths, and scan the desired frequencies or wavenumbers of light or radiation within a desired range, e.g., sequentially between the range of approximately 5700 $cm^{-1}$ and 6300 $cm^{-1}$, and in some embodiments between the range of approximately 5700 $cm^{-1}$ and 6000 $cm^{-1}$. In some embodiments, spectroscope 24 is operative to modulate the light or radiation received from light source 12 only through frequencies in the range of approximately 5700 $cm^{-1}$ and 6300 $cm^{-1}$, and in other embodiments only through frequencies between the range of approximately 5700 $cm^{-1}$ and 6000 $cm^{-1}$. The frequency increments may vary with the needs of the application. For example, in some embodiments, spectroscope 24 may scan the frequency range in 10 $cm^{-1}$ increments, whereas other embodiments may employ 100 $cm^{-1}$ increments. In some embodiments, only certain select frequencies within the desired range may be employed. In one form, spectroscope 24 is a dispersive diode array spectrometer or a variable filter spectrometer. In another form, the source 12 may be a tunable diode laser in which case spectroscope 24 is not required. In a particular form, spectroscope 24 is a Fourier transform infrared (FTIR) spectrum analyzer. A non-limiting example of a suitable spectroscope 24 is a commercially available FTIR spectrum analyzer, such as a MB3000 FTIR spectrum analyzer, manufactured by ABB Bomem of Quebec, Canada. In other embodiments, other spectroscopes or spectrum analyzers may be employed.

In one form, spectroscope 24 is disposed in the optical path between light source 12 and the sample cell being analyzed, e.g., sample cell 14, which avoids the spectral analysis of self emission by the sample, such as self emission in the long wavelength infrared region. In other embodiments, spectroscope 24 may be disposed in the optical path between the sample cell and detector 18, e.g., between the sample cell and filter 20 or between filter 20 and detector 16. Some embodiments may not employ a spectroscope. For example, in some embodiments, detector 16 may be constructed and operative to measure discrete frequencies or frequency bands without the need for a spectroscope to modulate or disperse the light or radiation emanating from light source 12. Some embodiments may only measure the loss of light at two discrete wavelengths or two discrete wavelength bands in order to ascertain the presence and quantity of hydrocarbon contaminant in the experimental sample in cell 14 thereby forgoing a detailed spectral analysis which would permit determining the type or chemical nature of hydrocarbon contaminant For example, a plurality of emitters such as discrete NIR lasers and/or LEDs and/or other light sources may be employed, wherein each emitter discharges light or radiation at a discrete frequency or frequency band in the range between approximately 5700 cm$^{-1}$ and 6300 cm$^{-1}$, or in some embodiments in the range between approximately 5700 cm$^{-1}$ and 6000 cm$^{-1}$.

Sample cell 14 is constructed to admit and hold a desired quantity of water as a sample S to be analyzed, e.g., either pure water (reference sample) or ostensibly contaminated water (experimental sample). During infrared analysis, sample cell 14 is disposed and positioned within the optical path to receive light generated by light source 12, e.g., as resolved or modulated by spectroscope 24. In one form, sample cell 14 is formed of quartz, i.e., has quartz windows 14A. In other embodiments, other infrared-transparent materials may be employed as windows 14A, e.g., materials that are transparent at frequencies in the range between approximately 5700 cm$^{-1}$ and 6300 cm$^{-1}$ in some embodiments or in the range between approximately 5700 cm$^{-1}$ and 6000 cm$^{-1}$ in other embodiments. In one form, sample cell 14 has an optical path length PL through the water sample of 5 mm or approximately 5 mm. In other embodiments, the path length may vary with the needs of the application, and may be, for example, in the range of 0.5 mm to 20 mm, or more preferably, in the range of 0.5 mm to 10 mm, or even more preferably, in the range of 2 mm to 8 mm. In other embodiments, the path length may be outside of these ranges. Sample cell 22 for embodiments so equipped is similar to sample cell 14.

Detector 16 is a light or electromagnetic radiation detector positioned to receive light or radiation transmitted through the sample and the sample cell. Detector 16 is operative to detect infrared radiation at least in the range between about 5700 cm$^{-1}$ and 6300 cm$^{-1}$ in some embodiments, and at least in the range between about 5700 cm$^{-1}$ and 6000 cm$^{-1}$ in other embodiments. Detector 16 may also detect light or radiation at other frequencies. Detector 16 is operative to generate an electronic signal in response to detecting the light or radiation, wherein the signal is indicative of the amplitude or strength of the light or radiation that is received by detector 16. An example of a suitable detector is a commercially available TE cooled extended wavelength InGaAs detector with a wavelength cutoff of at least 2000 nm. In some embodiments, detector 16 may be configured to resolve the frequencies of the IR radiation it detects.

Controller 18 is communicatively coupled to detector 16 and to spectroscope 24. Controller 18 is operative to control the modulation of the light by spectroscope 24. In some embodiments, controller 18 is also communicatively coupled to light source 12 and operative to control the output of light source 12. Controller 18 is operative to receive the signals output by detector 16, and to determine light loss through the sample cell in the range between about 5700 cm$^{-1}$ and 6300 cm$^{-1}$ using the signals. In one form, the light loss is denoted measured in terms of absorbance, e.g., such as the absorbance spectra of FIG. 6. In other embodiments, light loss may take other forms, including, for example, transmittance. In some embodiments, the light loss determination may be based on an initial calibration or reference value establishing initial characteristics, e.g., amplitudes at desired frequencies, of the light prior to introduction of the sample cell or of the sample into the optical path. In some embodiments, controller 18 is operative to determine light loss only in the range between about 5700 cm$^{-1}$ and 6300 cm$^{-1}$. In other embodiments, controller 18 may be operative to determine light loss only in the range between about 5700 cm$^{-1}$ and 6000 cm$^{-1}$. In still other embodiments, controller 18 may be operative to determine light loss at other frequencies as well.

Controller 18 is operative to determine a level of hydrocarbon contamination in the experimental water sample based on the light loss. In some embodiments, controller 18 is operative to compare light loss through the sample cell when filled with a reference water sample, e.g., pure water, to light loss through the sample cell when filled with an experimental water sample, i.e., the ostensibly contaminated water, to determine a light loss difference, and to determine the level of hydrocarbon contamination based on the difference. In various embodiments, controller 18 is operative to determine the level of hydrocarbon contamination based on the light loss in the range between about 5700 cm$^{-1}$ and 6300 cm$^{-1}$, or based on the light loss in the range between about 5700 cm$^{-1}$ and 6000 cm$^{-1}$, or based on only the light loss in the range between about 5700 cm$^{-1}$ and 6300 cm$^{-1}$, or based on only the light loss in the range between about 5700 cm$^{-1}$ and 6000 cm$^{-1}$. Controller 18 is operative to generate an output indicating the level of hydrocarbon contamination in the experimental water sample. The output may be, for example, displayed on a display (not shown) and/or may be a printed output.

Filter 20 is an optical filter. In one form, filter 20 is disposed in the optical path between the sample cell and detector 16. In one form, filter 20 is operative to block transmittance at wavenumbers above about 7000, i.e., frequencies above about 7000 cm$^{-1}$. In one form, filter 20 is a 1500 nm long wave filter. In other embodiments, other filters may be used in addition to or in place of a 1500 nm long wave filter. In some embodiments, a filter may be employed to also or alternatively block wavenumbers below the desired range, e.g., below about 5000-5500 cm$^{-1}$, which may in some embodiments be considered a part of filter 20.

A non-limiting example of methodology for performing infrared analysis for measuring hydrocarbon contamination in water includes directing light from light source 12 to and through the sample cell, for example, sample cell 14 containing the experimental water sample. The light includes near infrared radiation in a range between about 5700 cm$^{-1}$ and 6300 cm$^{-1}$. In some embodiments, the light includes near infrared radiation in a range between about 5700 cm$^{-1}$ and 6000 cm$^{-1}$. The light transmitted from or through the water sample is detected by detector 16. The light loss through the experimental water sample is then determined, i.e., the light loss in the range between about 5700 cm$^{-1}$ and 6300 cm$^{-1}$. In some embodiments, the light loss in the range between about 5700 cm$^{-1}$ and 6000 cm$^{-1}$ through the experimental water sample may be determined. In some embodiments, only the light loss in the range between about 5700 cm$^{-1}$ and 6300 cm$^{-1}$ or only the light loss in the range between about 5700 cm$^{-1}$ and 6000 cm$^{-1}$ may be determined.

The level of hydrocarbon contamination in the experimental water sample is then determined based on the light loss in the range between about 5700 cm$^{-1}$ and 6300 cm$^{-1}$. In some embodiments, the level of hydrocarbon contamination in the experimental water sample may be determined based on the light loss in the range between about 5700 cm$^{-1}$ and 6000 cm$^{-1}$. In other embodiments, the level of hydrocarbon contamination is determined based only on the light loss in the range between about 5700 cm$^{-1}$ and 6300 cm$^{-1}$, or in other embodiments, based only on the light loss in the range between about 5700 cm$^{-1}$ and 6000 cm$^{-1}$. An output indicating the level of hydrocarbon contamination is then generated, which may include, for example, displaying the level of contamination on a display (not shown) and/or printing the level of contamination using a printing device (not shown).

In some embodiments, the determination of the level of hydrocarbon contamination in the experimental sample is based not only on the light loss through the experimental sample, but also, the light loss through a reference sample, e.g., pure water. For example, light from the light source 12 may be directed through the reference water sample, e.g., pure water; and the light exiting the reference water sample may be detected. The light loss through the reference water sample in a range between about 5700 $cm^{-1}$ and 6300 $cm^{-1}$, or in some embodiments in a range between about 5700 $cm^{-1}$ and 6000 $cm^{-1}$ is then determined. The light loss through the reference water sample is subtracted from the light loss through the experimental water sample to generate a light loss difference. The level of hydrocarbon contamination in the experimental water sample is then determined based on the light loss difference in the range between about 5700 cm−1 and 6300 cm−1. In some embodiments, the level of hydrocarbon contamination in the experimental water sample may be determined based on the light loss difference in the range between about 5700 $cm^{-1}$ and 6000 $cm^{-1}$. In other embodiments, the level of hydrocarbon contamination is determined based only on the light loss difference in the range between about 5700 $cm^{-1}$ and 6300 $cm^{-1}$, or in other embodiments, based only on the light loss difference in the range between about 5700 $cm^{-1}$ and 6000 $cm^{-1}$. In still other embodiments, the level of hydrocarbon contamination is determined based on the light loss at only one or two discrete wavelengths or wavelength bands selected in the range between 5700 $cm^{-1}$ and 6300 $cm^{-1}$.

Various embodiments may include modulating the light prior to reaching the experimental sample (and the reference sample, for embodiments that employ a reference sample) or in some embodiments, the light after being transmitted from the experimental sample (and the reference sample, for embodiments that employ a reference sample). The modulation includes modulating or scanning through desired light frequencies in the range between about 5700 $cm^{-1}$ and 6300 $cm^{-1}$ or the range between about 5700 $cm^{-1}$ and 6000 $cm^{-1}$ in some embodiments, e.g., sequentially exposing the sample to different frequencies within the desired range. For example, the light may be modulated by a Fourier transform IR spectrum analyzer, e.g., as described above. In other embodiments, light source 12 may modulate the light with modulation frequencies unique to different wavelengths directed to the sample. In still other embodiments, the light may not be modulated—rather, detector 16 may be constructed and operative to resolve the amplitudes of frequency components transmitted through the sample and received at the detector. In some embodiments, the light or radiation is filtered prior to reaching detector 16 using filter 20, e.g., a 1500 nm long pass filter that is operative to block transmittance at wavenumbers above about 7000 $cm^{-1}$. In other embodiments, other filter parameters may be employed. Some embodiments may also filter out light or radiation below about 5000-5500 $cm^{-1}$. In other embodiments, other filter parameters may be employed.

In some embodiments, the level of contamination of the experimental sample is also determined by comparing the measured or determined light loss (or light loss difference, in some embodiments), with known light loss (e.g., known light loss values or profiles or characteristics) within the desired range (e.g., the range between about 5700 $cm^{-1}$ and 6300 $cm^{-1}$ or the range between about 5700 $cm^{-1}$ and 6000 $cm^{-1}$ in some embodiments). The determination of the level of contamination of the experimental sample is then based on the comparison. For example, the known light loss values or profiles may be obtained by measuring samples having known hydrocarbon contamination levels to obtain corresponding light loss characteristics in the range between about 5700 $cm^{-1}$ and 6300 $cm^{-1}$ (or the range between about 5700 $cm^{-1}$ and 6300 $cm^{-1}$, in some embodiments), yielding light loss characteristics associated with known hydrocarbon contamination levels or known light loss characteristics. The light loss characteristics (or light loss difference characteristics) associated with experimental samples may then be compared to the known light loss characteristics to determine the contamination level of the experimental sample, e.g., by comparison, and in some embodiments, with interpolation. An example of known light loss characteristics is illustrated in FIG. 6 and absorbance spectra of four (4) traces 62, 64, 66, 68 of 20 ppm isopropanol in water and three (3) traces 70, 72, 74 of absorbance for pure water, with a 5 mm sample path length.

In one form, the determination of the level of hydrocarbon contamination is made based on light loss (or light loss difference, in some embodiments) in the range between about 5700 $cm^{-1}$ and 6300 $cm^{-1}$ (or the range between about 5700 $cm^{-1}$ and 6000 $cm^{-1}$, in other embodiments). In some embodiments, the determination of the level of hydrocarbon contamination is made based only on light loss (or light loss difference, in some embodiments) in the range between about 5700 $cm^{-1}$ and 6300 $cm^{-1}$ (or only in the range between about 5700 $cm^{-1}$ and 6000 $cm^{-1}$, in other embodiments).

Embodiments of the present invention include a method for performing infrared analysis for measuring hydrocarbon contamination in water, comprising: providing light from a light source, the light including a near infrared (NIR) radiation output in a range between about 5700 $cm^{-1}$ and 6300 $cm^{-1}$; directing light from the light source through an experimental water sample; detecting the light transmitted from the experimental water sample; determining the light loss through the experimental water sample in the range between about 5700 $cm^{-1}$ and 6300 $cm^{-1}$; determining a level of hydrocarbon contamination in the experimental water sample based on the light loss in the range between about 5700 $cm^{-1}$ and 6300 $cm^{-1}$; and generating an output indicating the level of hydrocarbon contamination in the experimental water sample.

In a refinement, the method further comprises comparing the light loss with a known light loss in the range between about 5700 $cm^{-1}$ and 6300 $cm^{-1}$ associated with a known level of hydrocarbon contamination in water; and determining a level of hydrocarbon contamination based on the light loss and the known light loss.

In another refinement, the method further comprises modulating the light at switching frequencies uniquely associated with different wavelengths prior to the light reaching the experimental sample or after being transmitted from the experimental sample, wherein the modulation includes modulating through at least some frequencies in the range between about 5700 $cm^{-1}$ and 6300 $cm^{-1}$.

In yet another refinement, the method further comprises selecting the light source to have only one or two wavelengths or wavelength bands prior to the light reaching the experimental sample or after being transmitted from the experimental sample, wherein the wavelengths or wavelength bands occur in the range between about 5700 $cm^{-1}$ and 6300 $cm^{-1}$.

In still another refinement, the light source is a tunable laser or a plurality of lasers having different variable wavelengths, wherein the tunable laser permits tuning through at least some frequencies in the range between about 5700 $cm^{-1}$ and 6300 $cm^{-1}$, or wherein the plurality of lasers output light at least some frequencies in the range between about 5700 $cm^{-1}$ and 6300 $cm^{-1}$.

In yet still another refinement, the light source is one or more fixed wavelength lasers modulating the light at switching frequencies uniquely associated with different wavelengths that occur in the range between about 5700 cm−1 and 6300 cm−1.

In a further refinement, the infrared analysis is performed with a dispersive diode array spectrometer.

In a yet further refinement, the infrared analysis is performed with a dispersive scanning spectrometer.

In a still further refinement, the infrared analysis is performed using a Fourier transform infrared spectrum analyzer.

In a yet still further refinement, the method further comprises: directing light from the light source through a reference water sample; detecting the light exiting the reference water sample; determining the light loss through the reference water sample in a range between about 5700 cm−1 and 6300 cm−1; subtracting the light loss through the reference water sample from the light loss through the experimental water sample to generate a light loss difference; and determining the level of hydrocarbon contamination in the experimental water sample based on the light loss difference in the range between about 5700 cm−1 and 6300 cm−1.

In another further refinement, the method further comprises: comparing the light loss difference with a known light loss in the range between about 5700 cm−1 and 6300 cm−1 associated with a known level of hydrocarbon contamination in water; and determining the level of hydrocarbon contamination based on the comparison.

In yet another further refinement, the experimental water sample has a path length of between 0.5 and 10 millimeters.

In still another further refinement, the experimental water sample has a path length of approximately 5 millimeters.

In yet still another further refinement, the method further comprises filtering the light with a long wave filter operative to block transmittance at wavenumbers above about 7000 prior to detecting the light.

In an additional refinement, the method further comprises: measuring water samples with known hydrocarbon contamination levels to obtain known light loss characteristics in the range between about 5700 cm−1 and 6300 cm−1 associated with the known hydrocarbon contamination levels; and determining the level of hydrocarbon contamination in the experimental water sample based on the light loss and the known light loss characteristics.

Embodiments of the present invention include an apparatus for performing infrared analysis for measuring hydrocarbon contamination in water, comprising: a light source providing an output including a near infrared (NIR) spectral output in a range between about 5700 cm−1 and 6300 cm−1; a sample cell constructed to admit water and positioned to receive light from the light source, wherein the sample cell has a sample path length equal to or greater than about 0.5 millimeters; a detector positioned to receive light transmitted through the sample cell, wherein the detector is operative to detect radiation at least in the range between about 5700 cm−1 and 6300 cm−1; and a controller communicatively coupled to the detector, wherein the controller is operative to determine light loss through the sample cell in the range between about 5700 cm−1 and 6300 cm−1, to determine a level of hydrocarbon contamination in the experimental water sample based on the light loss in the range between about 5700 cm−1 and 6300 cm−1, and to generate an output indicating the level of hydrocarbon contamination in the experimental water sample.

In a refinement, the apparatus the apparatus is constructed to modulate the light at switching frequencies uniquely associated with different wavelengths prior to the light reaching the experimental sample or after being transmitted from the experimental sample, wherein the modulation includes modulating through at least some frequencies in the range between about 5700 cm−1 and 6300 cm−1.

In another refinement, the light source is constructed to yield only one or two wavelengths or wavelength bands prior to the light reaching the experimental sample or after being transmitted from the experimental sample; wherein the wavelengths or wavelength bands occur in the range between about 5700 cm−1 and 6300 cm−1.

In yet another refinement, the light source is a tunable laser or a plurality of lasers having different variable wavelengths, wherein the tunable laser permits tuning through at least some frequencies in the range between about 5700 cm−1 and 6300 cm−1, or wherein the plurality of lasers output light at least some frequencies in the range between about 5700 cm−1 and 6300 cm−1.

In still another refinement, the light source is one or more fixed wavelength lasers modulating the light at switching frequencies uniquely associated with different wavelengths that occur in the range between about 5700 cm−1 and 6300 cm−1.

In yet still another refinement, the infrared analysis is performed using a dispersive diode array spectrometer.

In a further refinement, the infrared analysis is performed using a dispersive scanning spectrometer In a yet further refinement, the infrared analysis is performed using a Fourier transform infrared spectrum analyzer.

In a still further refinement, the sample path length is between 0.5 and 10 millimeters.

In a yet still further refinement, the sample path length is 5 millimeters.

In another further refinement, the apparatus further comprises a light modulator positioned between the light source and the sample cell or between the sample cell and the detector, wherein the light modulator is operative to modulate the light through at least some light frequencies in the range between about 5700 cm−1 and 6300 cm−1.

In yet another further refinement, the light modulator is Fourier transform infrared spectrum analyzer.

In still another further refinement, the controller is operative to determine the level of hydrocarbon contamination in the experimental water sample based only on the light loss in the range between about 5700 cm−1 and 6300 cm−1.

In yet still another further refinement, the controller is operative to determine the level of hydrocarbon contamination in the experimental water sample based only on the light loss at only one or two discrete wavelengths or wavelength bands in the range between about 5700 cm−1 and 6300 cm−1.

In an additional refinement, the apparatus further comprises a long wave filter disposed between the sample cell and the detector, wherein the filter is operative to block transmittance at wavenumbers above about 7000 prior to detecting the light.

In another additional refinement, the controller is operative to compare light loss through the sample cell when filled with a reference water sample to light loss through the sample cell when filled with the experimental water sample.

In yet another additional refinement, the controller is operative to determine the level of hydrocarbon contamination in an experimental water sample based on a difference between the light loss through the sample cell when filled with a reference water sample and the light loss through the sample cell when filled with the experimental water sample.

Embodiments of the present invention include an apparatus for performing infrared analysis for measuring hydrocarbon contamination in water, comprising: a light source; a sample cell constructed to admit water and positioned to receive light from the light source, wherein the sample cell has a sample path length between about 2 millimeters and about 8 millimeters; a detector positioned to receive light transmitted through the sample cell, wherein the detector is operative to detect radiation at least in the range between about 5700 cm-1 and 6300 cm-1; a light modulator positioned between the light source and the sample cell or between the sample cell and the detector, wherein the light modulator is operative to modulate the light through at least one or two light frequencies or a range of light frequencies in the range between about 5700 cm-1 and 6300 cm-1; and a controller communicatively coupled to the detector, wherein the controller is configured to execute program instructions to determine light loss through the sample cell in the range between about 5700 cm-1 and 6300 cm-1, to determine a level of hydrocarbon contamination in the experimental water sample based only on the light loss in the range between about 5700 cm-1 and 6300 cm-1, and to generate an output indicating the level of hydrocarbon contamination in the experimental water sample.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

What is claimed is:

1. A method for performing infrared analysis for measuring hydrocarbon contamination in water, comprising:
    providing light from a light source, the light including a near infrared (NIR) radiation output in a range between about 5700 cm$^{-1}$ and 6300 cm$^{-1}$;
    directing light from the light source through an experimental water sample, wherein the experimental water sample has a path length of between 2 mm and 8 mm;
    detecting the light transmitted from the experimental water sample;
    determining the light loss through the experimental water sample in the range between about 5700 cm$^{-1}$ and 6300 cm$^{-1}$;
    determining a level of hydrocarbon contamination in the experimental water sample based on the light loss only in the range between about 5700 cm$^{-1}$ and 6300 cm$^{-1}$; and
    generating an output indicating the level of hydrocarbon contamination in the experimental water sample.

2. The method of claim 1, further comprising:
    comparing the light loss with a known light loss in the range between about 5700 cm$^{-1}$ and 6300 cm$^{-1}$ associated with a known level of hydrocarbon contamination in water; and
    determining a level of hydrocarbon contamination based on the light loss and the known light loss.

3. The method of claim 1, further comprising modulating the light at switching frequencies uniquely associated with different wavelengths prior to the light reaching the experimental sample or after being transmitted from the experimental sample, wherein the modulation includes modulating through at least some frequencies in the range between about 5700 cm$^{-1}$ and 6300 cm$^{-1}$.

4. The method of claim 1, further comprising selecting the light source to have only one or two wavelengths or wavelength bands prior to the light reaching the experimental sample or after being transmitted from the experimental sample, wherein the wavelengths or wavelength bands occur in the range between about 5700 cm$^{-1}$ and 6300 cm$^{-1}$.

5. The method of claim 1, wherein the light source is a tunable laser or a plurality of lasers having different variable wavelengths, wherein the tunable laser permits tuning through at least some frequencies in the range between about 5700 cm$^{-1}$ and 6300 cm$^{-1}$, or wherein the plurality of lasers output light at least some frequencies in the range between about 5700 cm$^{-1}$ and 6300 cm$^{-1}$.

6. The method of claim 1, wherein the light source is one or more fixed wavelength lasers modulating the light at switching, frequencies uniquely associated with different wavelengths that occur in the range between about 5700 cm$^{-1}$ and 6300 cm$^{-1}$.

7. The method of claim 1, wherein the infrared analysis is performed with a dispersive diode array spectrometer.

8. The method of claim 1, wherein the infrared analysis is performed with a dispersive scanning spectrometer.

9. The method of claim 1, wherein the infrared analysis is performed using a Fourier transform infrared spectrum analyzer.

10. The method of claim 1, further comprising:
    directing light from the light source through a reference water sample;
    detecting the light exiting the reference water sample;
    determining the light loss through the reference water sample in a range between about 5700 cm$^{-1}$ and 6300 cm$^{-1}$;
    subtracting the light loss through the reference water sample from the light loss through the experimental water sample to generate a light loss difference, wherein the experimental water sample has a path length of between 2 mm and 8 mm; and
    determining the level of hydrocarbon contamination in the experimental water sample based on the light loss difference only in the range between about 5700 cm$^{-1}$ and 6300 cm$^{-1}$.

11. The method of claim 10, further comprising:
    comparing the light loss difference with a known light loss in the range between about 5700 cm$^{-1}$ and 6300 cm$^{-1}$ associated with a known level of hydrocarbon contamination in water; and determining the level of hydrocarbon contamination based on the comparison.

12. The method of claim 1, wherein the experimental water sample has a path length of between 0.5 and 10 millimeters.

13. The method of claim 1, wherein the experimental water sample has a path length of approximately 5 millimeters.

14. The method of claim 1, further comprising filtering the light with a long wave filter operative to block transmittance at wavenumbers above about 7000 $cm^{-1}$ prior to detecting the light.

15. The method of claim 1, further comprising:
   measuring water samples with known hydrocarbon contamination levels to obtain known light loss characteristics in the range between about 5700 $cm^{-1}$ and 6300 $cm^{-1}$ associated with the known hydrocarbon contamination levels; and
   determining the level of hydrocarbon contamination in the experimental water sample based on the light loss and the known light loss characteristics.

16. An apparatus for performing infrared analysis for measuring hydrocarbon contamination in water, comprising:
   a light source providing an output including a near infrared (NIR) spectral output in a range between about 5700 $cm^{-1}$ and 6300 $cm^{-1}$;
   a sample cell constructed to admit water and positioned to receive light from the light source, wherein the sample cell has a sample path length equal to or greater than about 0.5 millimeters;
   a detector positioned to receive light transmitted through the sample cell, wherein the detector is operative to detect radiation at least in the range between about 5700 $cm^{-1}$ and 6300 $cm^{-1}$; and
   a controller communicatively coupled to the detector, wherein the controller is operative to determine light loss through the sample cell in the range between about 5700 $cm^{-1}$ and 6300 $cm^{-1}$, to determine a level of hydrocarbon contamination in the experimental water sample based the light loss only in the range between about 5700 $cm^{-1}$ and 6300 $cm^{-1}$, and to generate an output indicating the level of hydrocarbon contamination in the experimental water sample.

17. The apparatus of claim 16, wherein the apparatus is constructed to modulate the light at switching frequencies uniquely associated with different wavelengths prior to the light reaching the experimental sample or after being transmitted from the experimental sample, wherein the modulation includes modulating through at least some frequencies in the range between about 5700 cm−1 and 6300 cm−1.

18. The apparatus of claim 16, wherein the light source is constructed to yield only one or two wavelengths or wavelength bands prior to the light reaching the experimental sample or after being transmitted from the experimental sample; and wherein the wavelengths or wavelength bands occur in the range between about 5700 $cm^{-1}$ and 6300 $cm^{-1}$.

19. The apparatus of claim 16, wherein the light source is a tunable laser or a plurality of lasers having different variable wavelengths, wherein the tunable laser permits tuning through at least some frequencies in the range between about 5700 $cm^{-1}$ and 6300 $cm^{-1}$, or wherein the plurality of lasers output light at least some frequencies in the range between about 5700 $cm^{-1}$ and 6300 $cm^{-1}$.

20. The apparatus of claim 16, wherein the light source is one or more fixed wavelength lasers modulating the light at switching frequencies uniquely associated with different wavelengths that occur in the range between about 5700 $cm^{-1}$ and 6300 $cm^{-1}$.

21. The apparatus of claim 16, wherein the infrared analysis is performed using a dispersive diode array spectrometer.

22. The apparatus of claim 16, wherein the infrared analysis is performed using a dispersive scanning spectrometer.

23. The apparatus of claim 16, wherein the infrared analysis is performed using a Fourier transform infrared spectrum analyzer.

24. The apparatus of claim 16, wherein the sample path length is between 0.5 and 10 millimeters.

25. The apparatus of claim 24, wherein the sample path length is 5 millimeters.

26. The apparatus of claim 16, further comprising a light modulator positioned between the light source and the sample cell or between the sample cell and the detector, wherein the light modulator is operative to modulate the light through at least some light frequencies in the range between about 5700 $cm^{-1}$ and 6300 $cm^{-1}$.

27. The apparatus of claim 26, wherein the light modulator is a Fourier transform infrared spectrum analyzer.

28. The apparatus of claim 16, wherein the controller is operative to determine the level of hydrocarbon contamination in the experimental water sample based on the light loss at only one or two discrete wavelengths or wavelength bands in the range between about 5700 $cm^{-1}$ and 6300 $cm^{-1}$.

29. The apparatus of claim 16, further comprising a long wave filter disposed between the sample cell and the detector, wherein the filter is operative to block transmittance at wavenumbers above about 7000 $cm^{-1}$ prior to detecting the light.

30. The apparatus of claim 16, wherein the controller is operative to compare light loss through the sample cell when filled with a reference water sample to light loss through the sample cell when filled with the experimental water sample.

31. The apparatus of claim 16, wherein the controller is operative to determine the level of hydrocarbon contamination in an experimental water sample based on a difference between the light loss through the sample cell when filled with a reference water sample and the light loss through the sample cell when filled with the experimental water sample.

32. An apparatus for performing infrared analysis for measuring hydrocarbon contamination in water, comprising:
   a light source;
   a sample cell constructed to admit water and positioned to receive light from the light source, wherein the sample cell has a sample path length between about 2 millimeters and about 8 millimeters;
   a detector positioned to receive light transmitted through the sample cell, wherein the detector is operative to detect radiation at least in the range between about 5700 $cm^{-1}$ and 6300 $cm^{-1}$;
   a light modulator positioned between the light source and the sample cell or between the sample cell and the detector, wherein the light modulator is operative to modulate the light through at least some light frequencies in the range between about 5700 $cm^{-1}$ and 6300 $cm^{-1}$; and
   a controller communicatively coupled to the detector, wherein the controller is configured to execute program instructions to determine light loss through the sample cell in the range between about 5700 $cm^{-1}$ and 6300 $cm^{-1}$, to determine a level of hydrocarbon contamination in the experimental water sample based only on the light loss only in the range between about 5700 $cm^{-1}$ and 6300 $cm^{-1}$, and to generate an output indicating the level of hydrocarbon contamination in the experimental water sample.

33. The apparatus of claim 16, wherein the apparatus is constructed to determine trace levels of hydrocarbon contamination of 20 ppm or less.

* * * * *